United States Patent [19]

Eskamani et al.

[11] 4,450,059

[45] May 22, 1984

[54] PHOTOCHEMICAL DECARBOXYLATION OF A METAL SALT OF AN ALPHA-HYDROXY CARBOXYLIC ACID

[75] Inventors: Abolghassem Eskamani, Aurora; Helen D. Dernar, Parma; Rosemary Bartoszek-Loza, Solon, all of Ohio

[73] Assignee: The Standard Oil Company, Cleveland, Ohio

[21] Appl. No.: 528,763

[22] Filed: Sep. 2, 1983

[51] Int. Cl.$^3$ .............................................. B01J 19/12
[52] U.S. Cl. .............................................. 204/158 R
[58] Field of Search .................................. 204/158 R

[56] References Cited

U.S. PATENT DOCUMENTS

| | | | |
|---|---|---|---|
| 4,264,421 | 4/1981 | Bard et al. | 204/157.1 R |
| 4,303,486 | 12/1981 | Bard et al. | 204/162 R |

OTHER PUBLICATIONS

Euler et al., Biochemische Zeitschrift, vol. 51, pp. 97–106, 1913.
Baudisch, Biochemische Zeitschrift, vol. 103 (1920), pp. 59–62.
Muller, Biochemische Zeitschrift, vol. 178 (1926), pp. 77–78.
Burns, JACS, vol. 51 (1929), pp. 3,165–3,171.
Bard, Science, vol. 207 (1980), pp. 139–144.

*Primary Examiner*—Howard S. Williams
*Attorney, Agent, or Firm*—Thomas P. Schur; Joseph G. Curatolo; Larry W. Evans

[57] ABSTRACT

A process is provided for the photochemical decarboxylation of a metal salt of an alpha-hydroxy carboxylic acid to form the corresponding alcohol wherein the alpha-hydroxy carboxylic acid metal salt is exposed to light in the absence of a photosensitizing agent.

12 Claims, No Drawings

PHOTOCHEMICAL DECARBOXYLATION OF A METAL SALT OF AN ALPHA-HYDROXY CARBOXYLIC ACID

BACKGROUND OF THE INVENTION

The present invention relates to a process for the photo oxidative degradation of a metal salt of an alpha-hydroxy carboxylic acid. More specifically, the invention relates to a process for the photochemical decarboxylation of a metal salt of an alpha-hydroxy carboxylic acid in the absence of a photosensitizing agent to predominantly form the corresponding alcohol.

It has long been known to convert carboxylic acids such as lactic acid, which is an alpha-hydroxy carboxylic acid, to other useful chemicals such as ethanol, methanol, butanol, acetone, acetaldehyde, 2,3-butanediol, acetic acid, propionic acid, alpha-ketoglutaric acid, citric acid, glyoxylic acid, fumaric acid and other polyhydroxy and polycarboxylic compounds. Generally such conversion is accomplished by biological, thermochemical or photochemical means. Biological means, such as fermentation, are time-consuming processes. Thermochemical conversion of carboxylic acids to alcohols in the presence of a catalyst is disclosed in U.S. Pat. No. 3,013,038 to Blair et al. U.S. Pat. No. 3,251,878 to Pasky describes the thermochemical conversion of carboxylic acids to lower molecular weight oxygenated compounds using a metal catalyst. Thermochemical reactions require energy to raise the operating temperature of the process which increases the cost of a commercial operation. For this reason photochemical decarboxylation of alpha-hydroxy carboxylic acids may be preferred.

Euler and Ryd reported in *The Decomposition of Lactic Acid and Tannic Acid in Ultraviolet Light,* Biochemische Zeitschrift, Vol. 51, pp. 97–103, 1913, that lactic acid undergoes cleavage at 70° C. in the presence of ultraviolet light to form formic acid and acetaldehyde and that these products were in turn rapidly converted to ethanol and carbon dioxide. Euler and Ryd also reported using mineral acids, such as iron and manganese salts, to accelerate the cleavage of lactic acid. Muller disclosed the use of uranyl and iron salts to catalyze the conversion of lactic acid to ethanol. Mueller, R., *The Quantum Sensitivity of the Decomposition of Lactic Acid-Uranyl Sulfate,* Biochemische Zeitschrift, Vol. 178, pp. 77–78, 1926. Since that time uranyl salts have been popularly used in laboratory studies as photosensitizers to initiate and accelerate chemical reactions driven by light. Thus, uranyl salts enhance both thermochemical and photochemical reactions. However, uranyl salts are expensive and generally not used in commercial processes.

A photosensitizer such as a uranyl salt may be used in conjunction with another catalyst to enhance the performance of the catalyst for the photo-initated conversion of chemicals to desired photoproducts. The combination of photosensitizer and catalyst may produce high yields of a desired product and/or faster reaction rates of conversion when compared to the singular use of the photosensitizer or catalyst. However, processes utilizing both a photosensitizer and a catalyst generally are expensive to operate, as are processes that require a uranyl salt.

In addition, the production of chemicals by way of an alpha-hydroxy carboxylic acid intermediate is generally not a favored reaction path since it is a difficult and lengthy process to obtain yields of essentially pure alpha-hydroxy carboxylic acids, even though yields of the corresponding alcohol may be significant. Processes are known, however, in which the salt of an alpha-hydroxy carboxylic acid may be readily obtained but the photoreactivity of alpha-hydroxy carboxylic acid metal salts may not be similar to that of alpha-hydroxy carboxylic acids.

Thus, it would be a significant contribution to the field of photochemical carboxylic acid degradation to provide a process that produces a significant yield of desired product and/or fast reaction rates from an easily-derived carboxylic acid-based intermediate without requiring the use of both a photosensitizer and a catalyst. Therefore, it is an object of the present invention to provide a process for the photochemical decarboxylation of a metal salt of an alpha-hydroxy carboxylic acid having an improved yield of and/or reaction rate for the formation of the corresponding alcohol.

The above object and other objects of the present invention, together with the advantages thereof, will become apparent from the following specification and appended claims.

SUMMARY OF THE INVENTION

The present invention relates to a process for the photochemical decarboxylation of a metal salt of an alpha-hydroxy carboxylic acid to form the corresponding alcohol wherein the alpha-hydroxy carboxylic acid metal salt is exposed to light in the absence of a photosensitizing agent.

Metal salts of alpha-hydroxy carboxylic acids may be derived by reacting a metal base, preferably a metal oxide base, with a solution containing an alpha-hydroxy carboxylic acid therein or may occur as an intermediate in other processes such as the thermal conversion of biomass. Such salts may be converted by the process of this invention to chemicals such as alcohols, acids, diols, aldehydes and lactones which can be used as fuels and/or feedstocks for other chemical processes.

The invention also relates to a process for the photochemical decarboxylation of a metal salt of an alpha-hydroxy carboxylic acid wherein the alpha-hydroxy carboxylic acid metal salt may be represented by the formula:

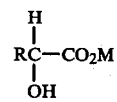

wherein
R is hydrogen or an alkyl, alkenyl, aryl, alkaryl, cycloalkyl, or cycloalkenyl having from 1 to about 20 carbon atoms, and
M is a metal selected from the group consisting of Group IVA, VA, VIA, VIIA and VIIIA elements, Ce, Al, Ca, Mg and Sn;
and wherein the metal salt is initially present in a solution at a concentration of from about 0.01 percent to about 50 percent by weight based on the total weight of the solution, and is exposed to light having a wavelength of from about 2,200 Å to about 14,000 Å, at a temperature of from about 0° C. to about 100° C., and in the absence of a photosensitizing agent.

DETAILED DESCRIPTION OF THE INVENTION

The metal salt of an alpha-hydroxy carboxylic acid in accordance with the invention may be represented by the formula:

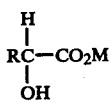

wherein
R is hydrogen or an alkyl, alkenyl, aryl, alkaryl, cycloalkyl having from 1 to about 20 carbon atoms, and
M is a metal selected from the group consisting of Group IVA, VA, VIA, VIIA and VIIIA elements, Ce, Al, Ca, Mg and Sn.

Preferably R is an alkyl, alkenyl, aryl, alkaryl, cycloalkyl or cycloalkenyl having from 1 to about 12 carbon atoms. Alpha-hydroxy carboxylic acids which can be used in the inventive process include but are not limited to mandelic acid, alpha-hydroxy isobutyric acid, alpha-ethyl-alpha-hydroxy butyric acid, alpha-hydroxy-alpha-methyl butyric acid, alpha-isopropyl-mandelic acid, lactic acid, benzylic acid, phenyllactic acid and mixtures thereof.

Preferably M is at least one member selected from the group consisting of zirconium, calcium, cobalt, nickel, manganese, molybdenum, niobium, cerium, tin and vanadium. Most preferably, M is selected from the group consisting of calcium, manganese, cobalt, nickel and zirconium.

Optimally, R is $CH_3$ and the carboxylic acid metal salt is a metal lactate such as zirconium lactate, calcium lactate, cobalt lactate, nickel lactate, manganese lactate, molybdenum lactate, niobium lactate, cerium lactate, tin lactate and vanadium lactate. The valence number of the metal in the metal lactate appears to influence the ethanol yield. A higher valence number has been found to be related to higher alcohol yields. Preferably the valence number of the metal in the alpha-hydroxy carboxylic acid metal salt is at least 4.

The alpha-hydroxy carboxylic acid metal salt is dissolved in a media so that the concentration of metal salt in solution ranges from about 0.01 percent to about 50 percent by weight based on the total weight of the solution. At less than 0.01 percent concentration the formation of alcohol is negligible. At more than 50 percent concentration of metal salt, competing by-product reactions reduce the effective yield of alcohol. For optimum alcohol yields and reaction rates it is preferred that the concentration of the alpha-hydroxy carboxylic acid metal salt in solution range from about 0.5 percent to about 10 percent by weight, based on the weight of the solution, and it is most preferred to have an alpha-hydroxy carboxylic acid metal salt concentration of from about 1 percent to about 5 percent by weight based on the total weight of the solution. Preferably the media is aqueous, although any media in which the alpha-hydroxy carboxylic acid salt is soluble and which does not substantially block high energy light radiation may be used such as acetonitrile.

The metal salt solution is irradiated with a light source which may be solar or artificial and which preferably contains light having wavelengths in the range of from about 2,200 Å to about 14,000 Å. In accordance with the invention, in the absence of a photosensitizing agent or catalyst, the alpha-hydroxy carboxylic acid metal salt is photochemically decarboxylated primarily into carbon dioxide and the corresponding alcohol, as well as minor yields of other alcohols, acids, diols, aldehydes, lactones and other hydrocarbon materials. The metal remains in solution and can be reclaimed by well-known means such as by using a complexing agent.

The process may proceed under a wide range of temperatures, pressures and atmospheres and still provide the photo-induced decarboxylation of alpha-hydroxy carboxylic acids to the corresponding alcohols. Optimum reaction conditions will be dependent on the particular reactants used. Preferably the photo-induced decarboxylation of alpha-hydroxy carboxylic acids occurs at temperatures of from about 0° C. to about 100° C., pressures of from about 1 atmosphere to about 10 atmospheres and under an oxidative or inert atmosphere. More preferred, the photochemical reaction occurs at from about 0° C. to about 50° C., from about 1 to about 3 atmospheres, and under an atmosphere of nitrogen, helium, argon, oxygen or air. Optimally, alpha-hydroxy carboxylic acids are photochemically converted to the corresponding alcohols in the presence of semiconductor catalyst materials at temperatures of from about 20° C. to about 30° C., at about atmospheric pressure and under an atmosphere of nitrogen, argon or air.

Any light source with spectral energy ranging from far ultraviolet through middle ultraviolet and near ultraviolet and also through the visible and infrared range, that is from about 2,200 Å to about 14,000 Å, may be employed as the light source for this invention. It is preferred to utilize a light source where a substantial concentration of radiated energy lies in the range of from about 2,200 Å to about 7000 Å, and most preferred to utilize a light source which emits a substantial concentration of radiated energy at from about 2,200 Å to about 4,000 Å.

The photochemical decarboxylation of alpha-hydroxy carboxylic acid metal salt compounds occurs over an irradiation period of up to about 24 hours. It is preferred to permit the photochemical reactions to occur for from between about 16 and about 20 hours. The reaction time is not a critical parameter but is dependent on the concentration of the alpha-hydroxy carboxylic acid in solution, the catalyst and concentration of the catalyst and the intensity of the irradiation. This photo-induced process may take place as a batch process or as a continuous process.

A reaction catalyst which has a preference for the formation of a specific compound such as the conversion of lactic acid to ethanol may be employed in the alpha-hydroxy carboxylic acid metal salt solution to further increase yield, but is not necessary for purposes of this invention. An example of a known reaction catalyst that improves the yield of alcohol from alpha-hydroxy carboxylic acids is cobalt nitrate.

Surprisingly, it has been found that the use of known photosensitizing agents, such as uranyl acetate, reduces the conversion of metal salts of alpha-hydroxy carboxylic acids to alcohols. Hence, contrary to prior art teachings, photosensitizing agents are not useful for the photo-oxidative degradation of a metal salt of an alpha-hydroxy carboxylic acid.

EXAMPLES

The above-described invention may be more clearly understood by the following examples which are not intended to be limitative of the invention in any way. The following examples measure ethanol yield from the photo-oxidative degradation of lactic acid and various alpha-hydroxy carboxylic acid metal salts with and without a photosensitizing agent being present in the reaction solution. It is understood that the use of lactic acid and metal lactates in the examples are representative of alpha-hydroxy carboxylic acids and metal salts of alpha-hydroxy carboxylic acids, and that other alpha-hydroxy carboxylic acids and metal salts of alpha-hydroxy carboxylic acids would react in a similar manner.

Solutions of lactic acid and various lactic acid metal salts were prepared by placing the lactic acid or lactic acid metal salt in distilled water so that the concentration of lactic acid or metal lactate ranged from about 0.875 percent to about 9 percent by weight based on the total weight of the solution. Similar solutions were also prepared in which 0.1 percent by weight, based on the total weight of the solution, of a photosensitizing agent, uranyl acetate, was added.

Each solution was then subjected to a light source in the following manner:

About 350 ml. of the solution to be tested was poured into a photochemical reaction vessel equipped with a quartz immersion well. The temperature of the solution was regulated and maintained at between about 23° C. and about 28° C. through the use of cooling water circulating through the jacketed quartz immersion well. The solution was kept agitated by the use of a magnetic stirrer and a motor-driven mixer. Nitrogen gas was admitted into the reaction solution to provide a relatively oxygen-free environment. The nitrogen flow rate averaged about 30 ml/min.

A light source was disposed in the quartz immersion well. The light source had the following spectral energy distribution (recorded in watts):

| Far UV | 2200–2,800Å | 29.2 watts |
| Middle UV | 2800–3,200Å | 32.8 watts |
| Near UV | 3200–4,000Å | 32.9 watts |
| Visible | 4,000–10,000Å | 87.2 watts |
| Infrared | 10,000–14,000Å | 20.6 watts |

Each solution was allowed to react under the above described conditions for about 13 hours, at which time the percent ethanol yield was determined. The results are presented herebelow in Table 1. As can be seen from Examples 1 and 2 in the Table, addition of uranyl salts to lactic acid demonstrates a photosensitizing effect with respect to the amount of ethanol produced, the photosensitizer increasing the amount of ethanol formed by about 70 percent. However, as shown in Examples 3–12, when uranyl acetate photosensitizing agent is added to an alpha-hydroxy carboxylic acid metal salt solution a substantial decrease in the alcohol yield is observed as compared to the alcohol yield of solutions wherein no photosensitizing agent was present.

Table 1 also demonstrates the relationship between valence number and conversion selectivity for the corresponding alcohol. The valence number of the metals in Examples 3–10 was two while the valence number of zirconium, the metal used in Examples 11 and 12, was four. A significant increase in alcohol formation is seen with the higher valence number.

It is understood that modifications and changes of the foregoing examples may be made without departing from the spirit of the present invention. The selection of the alpha-hydroxy carboxylic acid metal salts, the products derived from the photo-induced decarboxylation thereof and reactant conditions can be determined from the preceeding specification without departing from the spirit of the invention herein disclosed and described; the scope of the invention including modifications and variations that fall within the scope of the appended claims.

TABLE 1
PHOTOSENSITIZER EFFECT ON ALCOHOL YIELD

| EXAMPLE | SOLUTION (WEIGHT PERCENT IN AQUEOUS SOLUTION) | PHOTOSENSITIZER | PERCENT ETHANOL YIELD |
|---|---|---|---|
| 1 | 9% Lactic Acid | None | 13 |
| 2 | 9% Lactic Acid | 0.1% Uranyl Acetate | 22 |
| 3 | 5% Calcium Lactate | None | 4 |
| 4 | 5% Calcium Lactate | 0.1% Uranyl Acetate | 1 |
| 5 | 5% Manganese Lactate | None | 0.6 |
| 6 | 5% Manganese Lactate | 0.1% Uranyl Acetate | 0.8 |
| 7 | 0.875% Cobalt Lactate | None | 2 |
| 8 | 0.875% Cobalt Lactate | 0.1% Uranyl Acetate | 1 |
| 9 | 1% Nickel Lactate | None | 1 |
| 10 | 1% Nickel Lactate | 0.1% Uranyl Acetate | N.M.* |
| 11 | 1% Zirconium Lactate | None | 14 |
| 12 | 1% Zirconium Lactate | 0.1% Uranyl Acetate | 7 |

*N.M. — Not Measured

We claim:

1. A process for the photochemical decarboxylation of a metal salt of an alpha-hydroxy carboxylic acid wherein the alpha-hydroxy carboxylic acid metal salt may be represented by the formula:

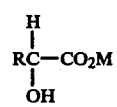

wherein;

R is hydrogen or an alkyl, alkenyl, aryl, alkaryl, cycloalkyl or cycloalkenyl having 1 to about 20 carbon atoms; and M is a metal selected from the group consisting of Group IB, IIB, IIIB, IVB, VB, VIB, VIIB, and VIIIB elements, Ce, Al, Ca, Mg and Sn;

and wherein said alpha-hydroxy carboxylic acid metal salt is present in an aqueous solution at a concentration of from about 0.01 percent to about 50 percent by weight based on the total weight of the solution, and is exposed to light at a temperature between about 0° C. and about 100° C. in the absence of a photosensitizing agent.

2. The process of claim 1 wherein R is selected from the group consisting of alkyls, alkenyls, aryls, alkaryls, cycloalkyls and cycloalkenyls having from 1 to about 12 carbon atoms.

3. The process of claim 1 wherein R is CH$_3$ and M is selected from the group consisting of Zr, Ca, Co, Ni, Mn, Mo, Nb, Ce, Sn and V.

4. The process of claim 1 wherein M is at least one member selected from the group consisting of Ca, Mn, Co, Ni and Zr.

5. The process of claim 1 wherein R is CH$_3$.

6. The process of claim 1 wherein said light includes a range of wavelengths of between about 2,000 Å and about 14,000 Å.

7. The process of claim 1 wherein said light includes a range of wavelengths of between about 2,000 Å and about 4,000 Å.

8. The process of claim 1 wherein M has a valence number of at least 4.

9. The process of claim 1 wherein said process occurs at a temperature of between about 0° C. and about 50° C.

10. The process of claim 1 wherein said process occurs at a temperature of between about 20° C. and about 30° C.

11. The process of claim 1 wherein the alpha-hydroxy carboxylic acid metal salt is in an aqueous solution at a concentration of from about 0.5 percent to about 10 percent by weight based on the total weight of the solution.

12. The process of claim 1 wherein the alpha-hydroxy carboxylic acid metal salt is in an aqueous solution at a concentration of from about 1.0 percent to about 5.0 percent by weight based on the total weight of the solution.

* * * * *